(12) United States Patent
Ferrante et al.

(10) Patent No.: US 6,320,656 B1
(45) Date of Patent: Nov. 20, 2001

(54) HIGH NUMERICAL APERTURE FLOW CYTOMETER AND METHOD OF USING SAME

(75) Inventors: Anthony A. Ferrante, Medford; W. Peter Hansen, Canaan, both of NY (US)

(73) Assignee: Idexx Laboratories, Inc., Westbrook, ME (US)

( * ) Notice: Subject to any disclaimer, the term of this patent is extended or adjusted under 35 U.S.C. 154(b) by 0 days.

(21) Appl. No.: 09/507,515

(22) Filed: Feb. 18, 2000

(51) Int. Cl.$^7$ ............................ G01N 21/00; G01N 33/48
(52) U.S. Cl. ...................... 356/339; 356/343; 356/73; 436/63
(58) Field of Search .................................. 356/337, 336, 356/338, 339, 340, 343, 73, 39, 40; 436/63, 10, 149, 172, 43, 54, 180, 522, 523; 422/63, 67, 73, 82.08

(56) References Cited

U.S. PATENT DOCUMENTS

| | | | |
|---|---|---|---|
| 4,565,448 | * 1/1986 | Abbott et al. | 359/336 |
| 4,606,636 | 8/1986 | Monin et al. | 356/338 |
| 4,818,103 | 4/1989 | Thomas et al. | 356/72 |
| 4,954,715 | 9/1990 | Zöld | 356/72 |
| 5,017,497 | * 5/1991 | Grooth et al. | 356/337 |
| 5,179,026 | * 1/1993 | Matsuda et al. | 436/63 |
| 5,264,369 | * 11/1993 | Sakata et al. | 436/63 |
| 5,308,772 | * 5/1994 | Sakata et al. | 436/63 |
| 5,408,307 | * 4/1995 | Yamamoto et al. | 356/73 |
| 5,432,601 | * 7/1995 | Tanaka et al. | 356/246 |
| 5,467,189 | * 11/1995 | Kreikebaum et al. | 356/336 |
| 5,631,165 | 5/1997 | Chupp et al. | 436/43 |
| 5,650,847 | 7/1997 | Maltsev et al. | 356/336 |
| 5,747,343 | * 5/1998 | Tsuchiya et al. | 436/63 |
| 5,940,177 | * 8/1999 | Esser et al. | 356/338 |

* cited by examiner

*Primary Examiner*—Hoa Q. Pham
(74) *Attorney, Agent, or Firm*—Lyon & Lyon LLP (57) ABSTRACT

The high numerical aperture flow cytometer of the present invention includes a flow cell and a laser input. The laser input emits a beam of light that is oriented substantially orthoganilly to the flow of blood cells through the flow cell such that laser light impinges upon the blood cells as they pass through the flow cell. A portion of the beam from the laser input that impinges upon the blood cells in the flow cell is scattered at a substantially right angle to the beam of laser input ("right angle scatter"). A second portion of the beam from the laser input that impinges upon the cells in the flow cell is scattered at a much lower angle than 90°. This scatter is termed "low angle forward scatter light" and has an angle of from about 2° to about 5° from the orientation of the original beam from laser input. A right angle scatter light detector is oriented to receive the previously mentioned right angle scatter light. A low angle forward scatter light detector is oriented to capture the previously mentioned low angled forward scatter light oriented at about 2° to about 5° from the beam of the laser input.

20 Claims, 12 Drawing Sheets

HIGH NUMERICAL APERTURE FLOW CYTOMETER AND METHOD OF USING SAME

FIELD OF THE INVENTION

The present invention relates to particle discrimination by light scattering, and more particularly to a flow cytometer and method therefore that discriminates particles employing a high numerical aperture. Numerical aperture is defined as the refractive index of the medium through which light is collected multiplied by the sine value of one-half of the angle of light collection.

BACKGROUND OF THE INVENTION

The discrimination of particles is useful in numerous clinical assays including ascertaining the types and numerical quantity of cells in blood, ascertaining invasive particles in a fluid sample, such as bacteria and virus, and quantifying the density and volume of cells in a fluid sample.

Figure 1:
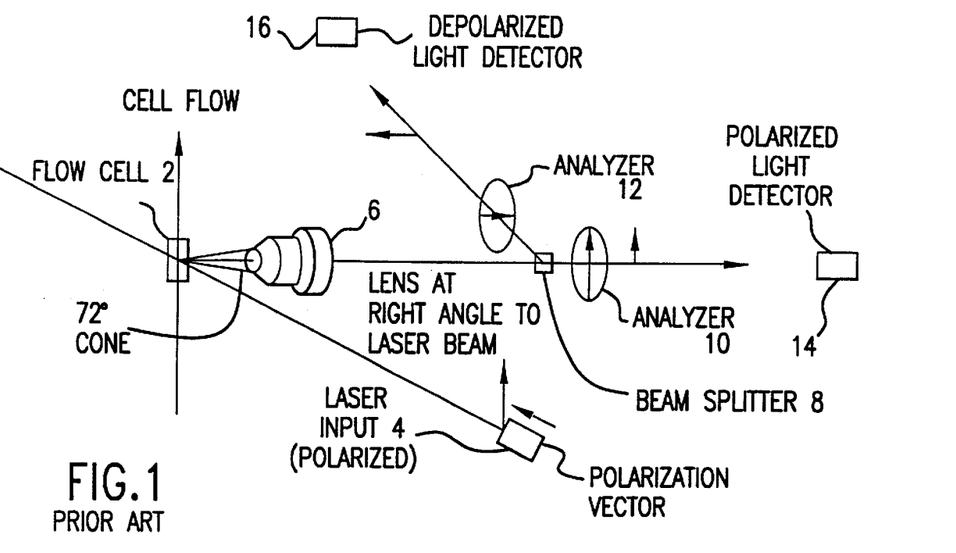
FIG. 1 is a schematic representation of the electro-optical components of prior art.

One method of the above is disclosed in U.S. Pat. No. 5,017,497 issued to de Grooth et al. FIG. 1 of the present application illustrates the apparatus disclosed '497 Patent. Referring to FIG. 1, the '497 Patent discloses a flow cell 2 through which cells from, for example, blood or the like, flow substantially one by one therethrough. A laser input 4 emits a polarized beam of laser light that is oriented substantially orthogonally to the flow of blood cell through flow cell 2 such that the polarized laser light impinges upon the blood cells as they pass through flow cell 2. By "polarized" it is meant that the plane of the electric field oscillation of the laser light is uniform. An optical lens 6 has an aperture which limits the cone of scattered light from the blood cells that can be collected to 72° or less. The central axis of the cone of lens 6 is 90° to both the path of the polarized laser light and the flow of blood cells through flow cell 2. The scattered light emanating from lens 6 is collimated in a matter known in the art. The scattered light now has a mixed polarization that is characteristic of the cell type. The light next passes through a beam splitter 8 that divides the light into two separate beams. A first light beam, substantially concentric with the light beam that originally emanated from lens 6, passes through first polarization analyzer 10. Polarization analyzer 10 is configured to pass therethrough only polarized light having a vector the same as the original laser light. The second beam emanating from beam splitter 8 is oriented substantially perpendicular to the orientation of the first beam emanating from beam splitter 8. This second beam enters second polarization analyzer 12. Second polarization analyzer 12 is configured to pass therethrough only light having a polarization vector substantially orthogonal to the polarization vector of the other beam from beam splitter 8 that passed through first polarization analyzer 10. The beams that pass through first polarization analyzer 10 and second polarization 12 enter polarized detector 14 and depolarized light detector 16, respectively. The ratio of the outputs of polarized light detector 14 and depolarized light detector 16, based on intensity, provide the depolarization ratio.

Figure 4:
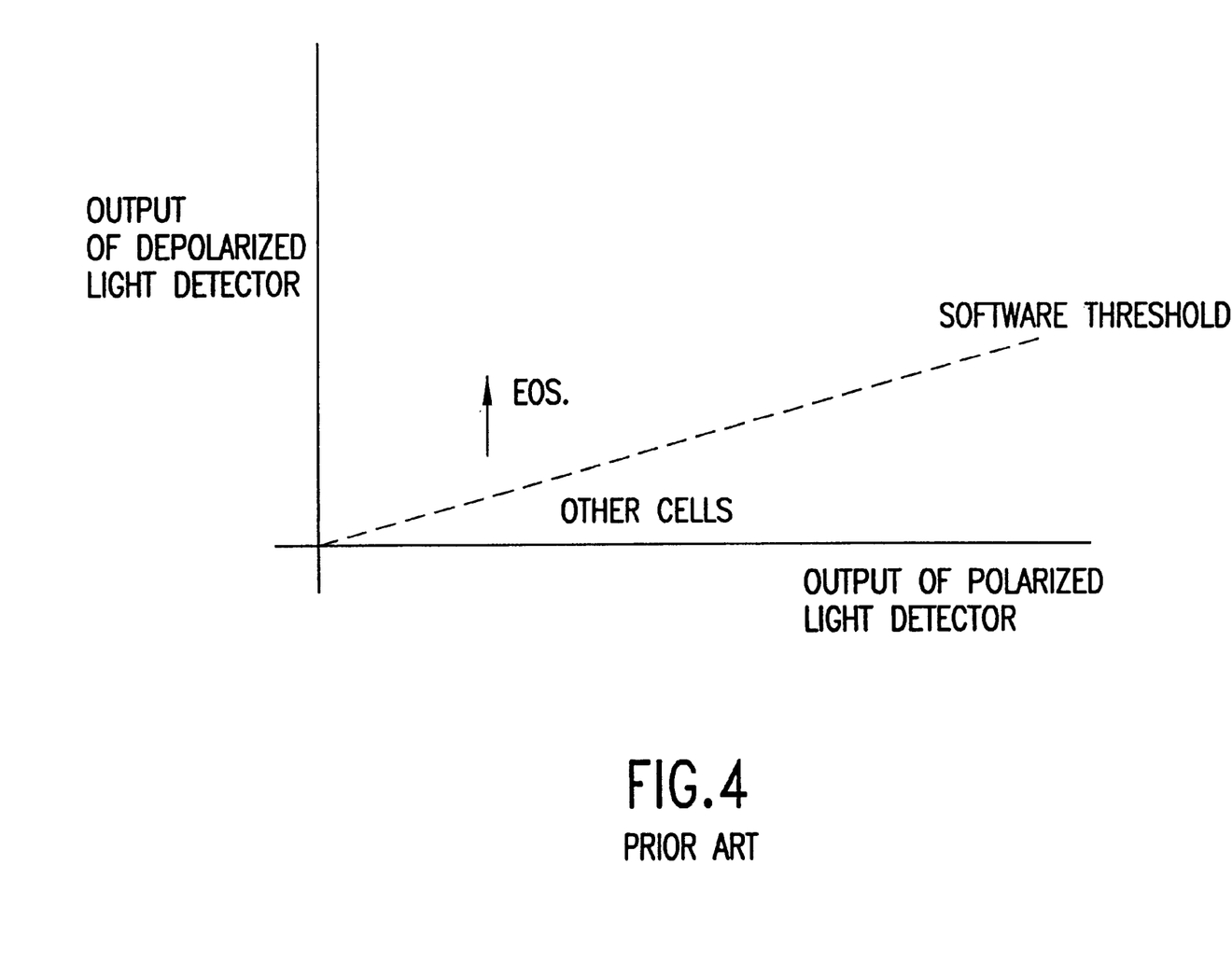
FIG. 4 is a graphical representation of the separation of eosinophils and other white blood cell components based on light scatter in the prior art.
Figure 6A:
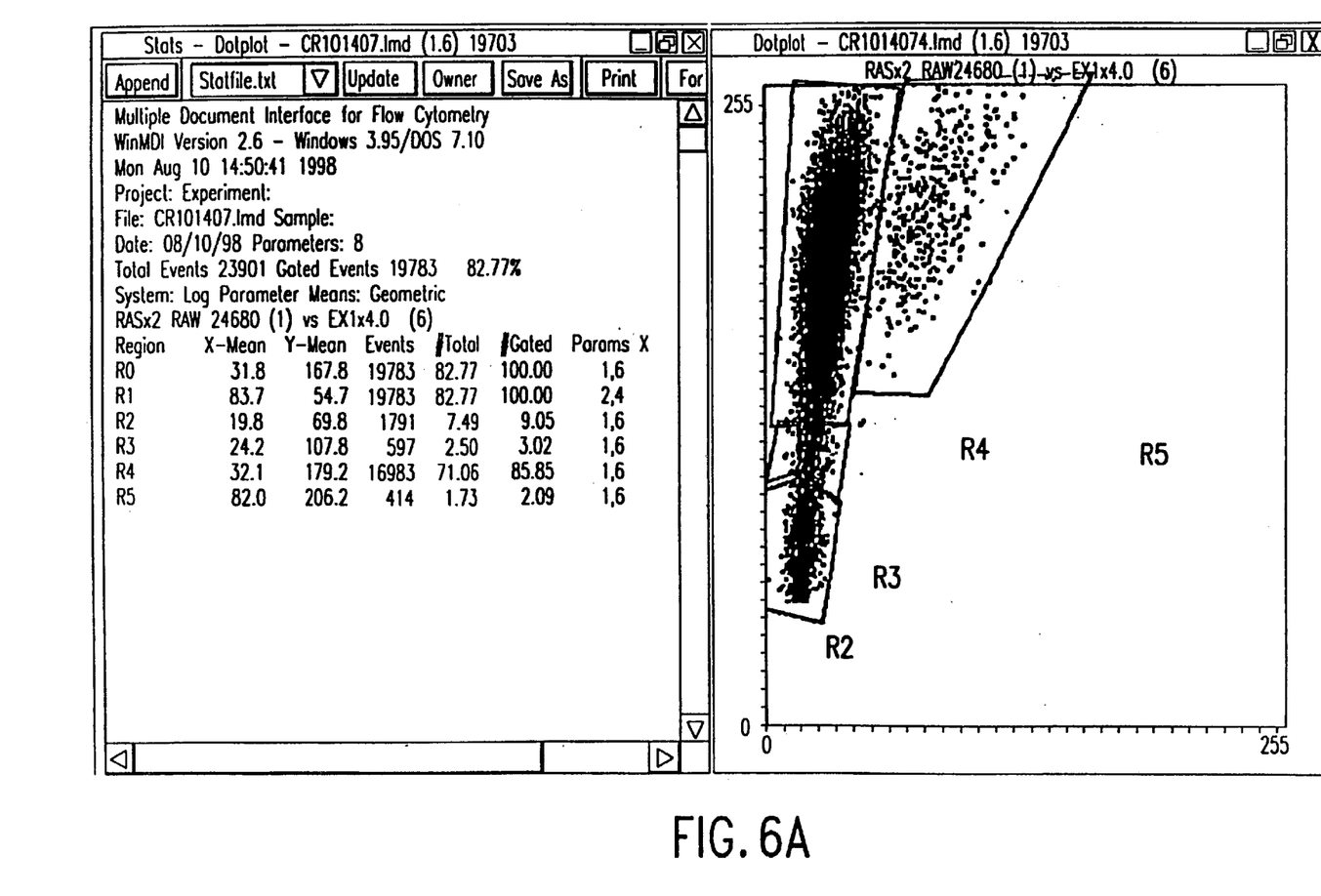
FIG. 6A is a graphical representation of 2% canine eosinophil data employing the prior art.
Figure 6B:
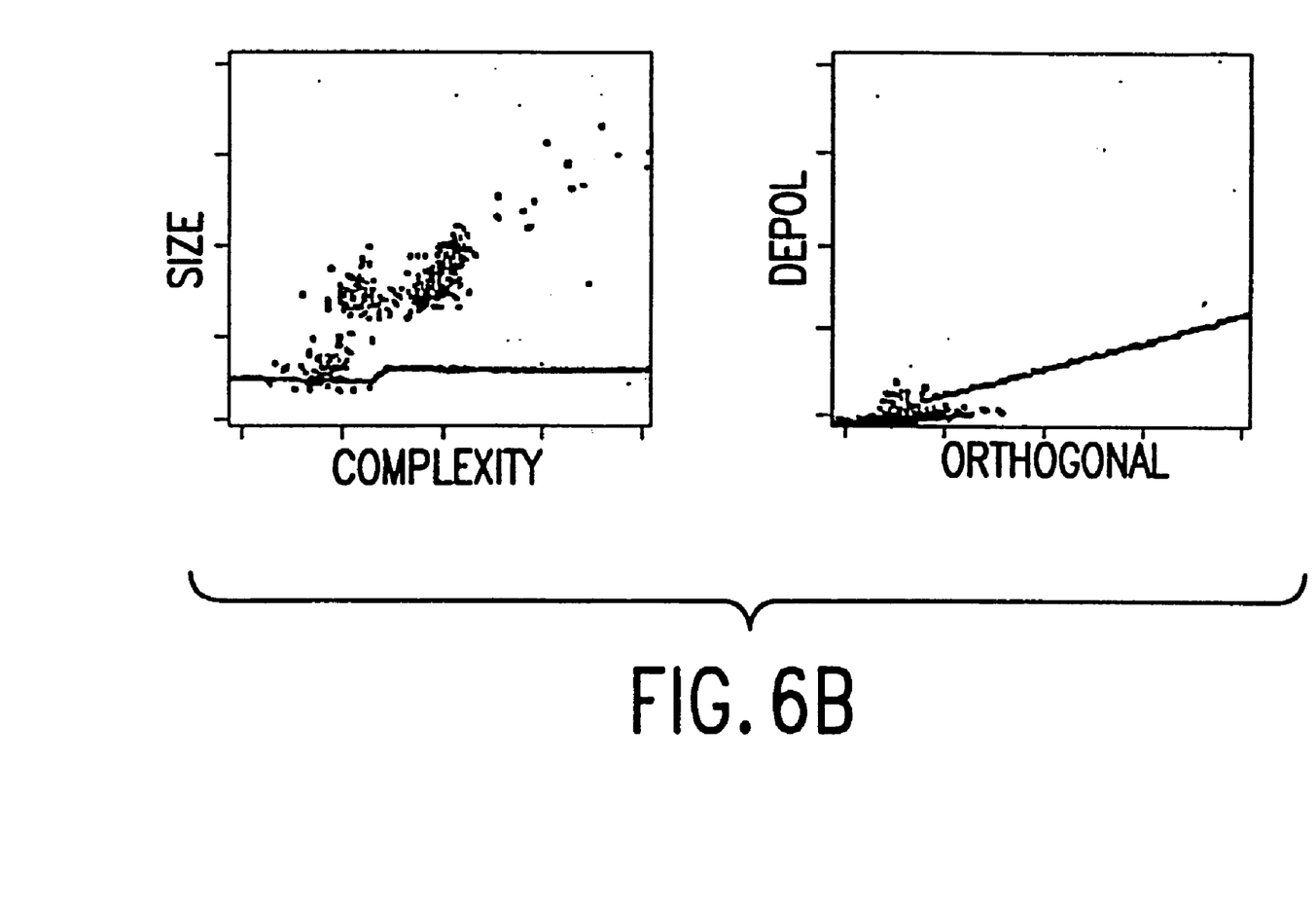
FIG. 6B is a graphical representation of 2% canine eosinophil data employing the present invention.
Figure 7A:
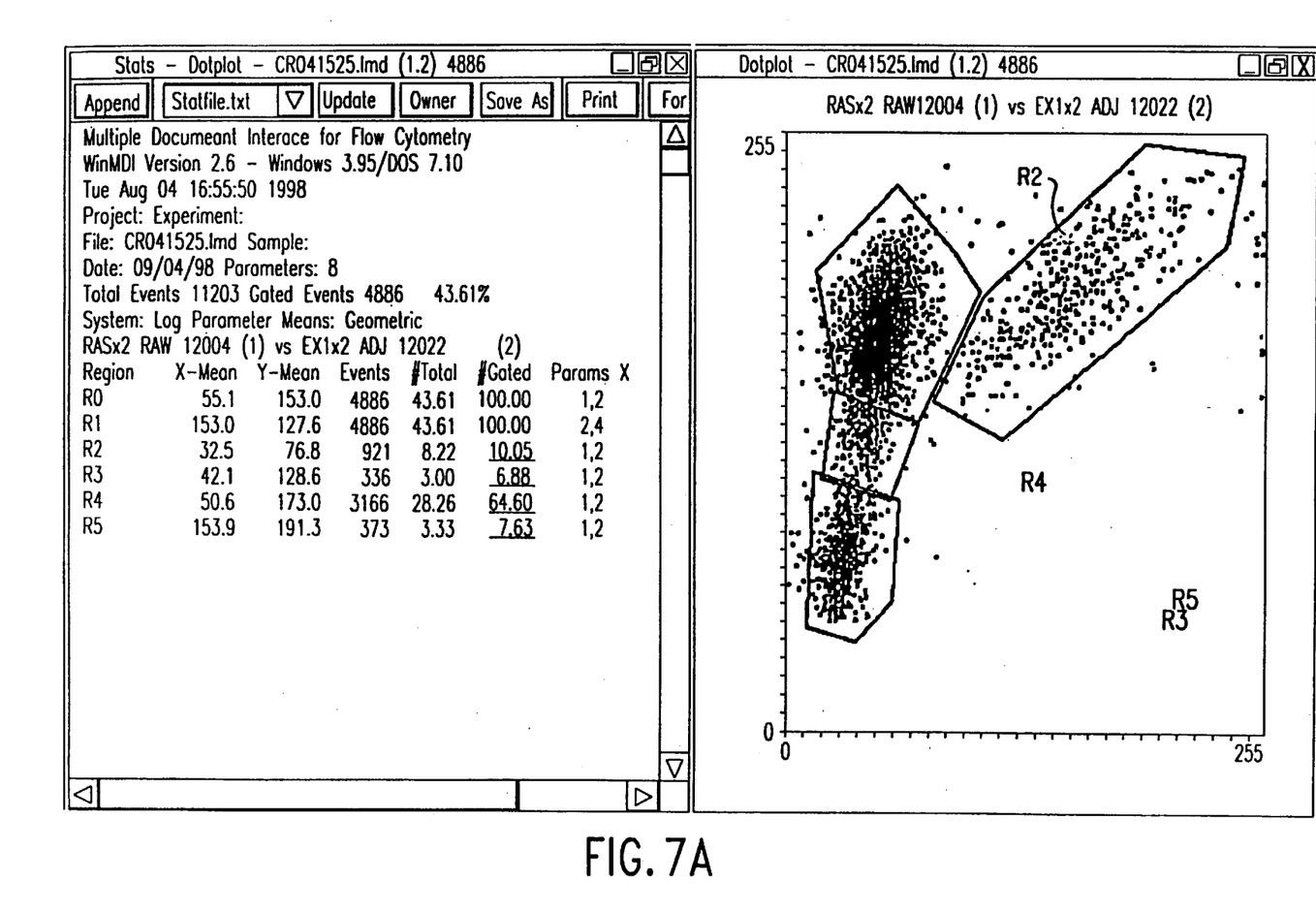
FIG. 7A is a graphical representation of 8% canine eosinophil data employing the prior art.
Figure 7B:
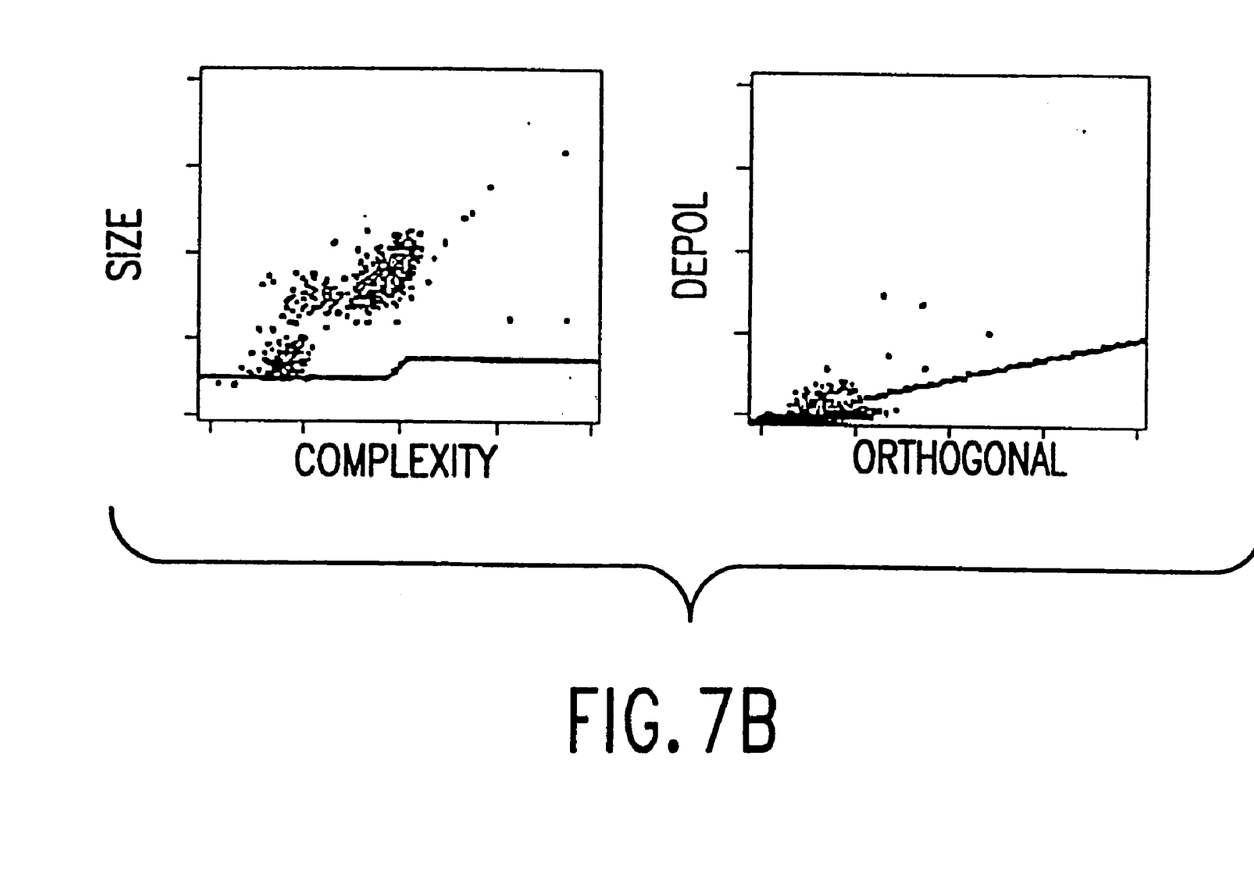
FIG. 7B is a graphical representation of 8% canine eosinophil data employing the present invention.
Figure 8A:
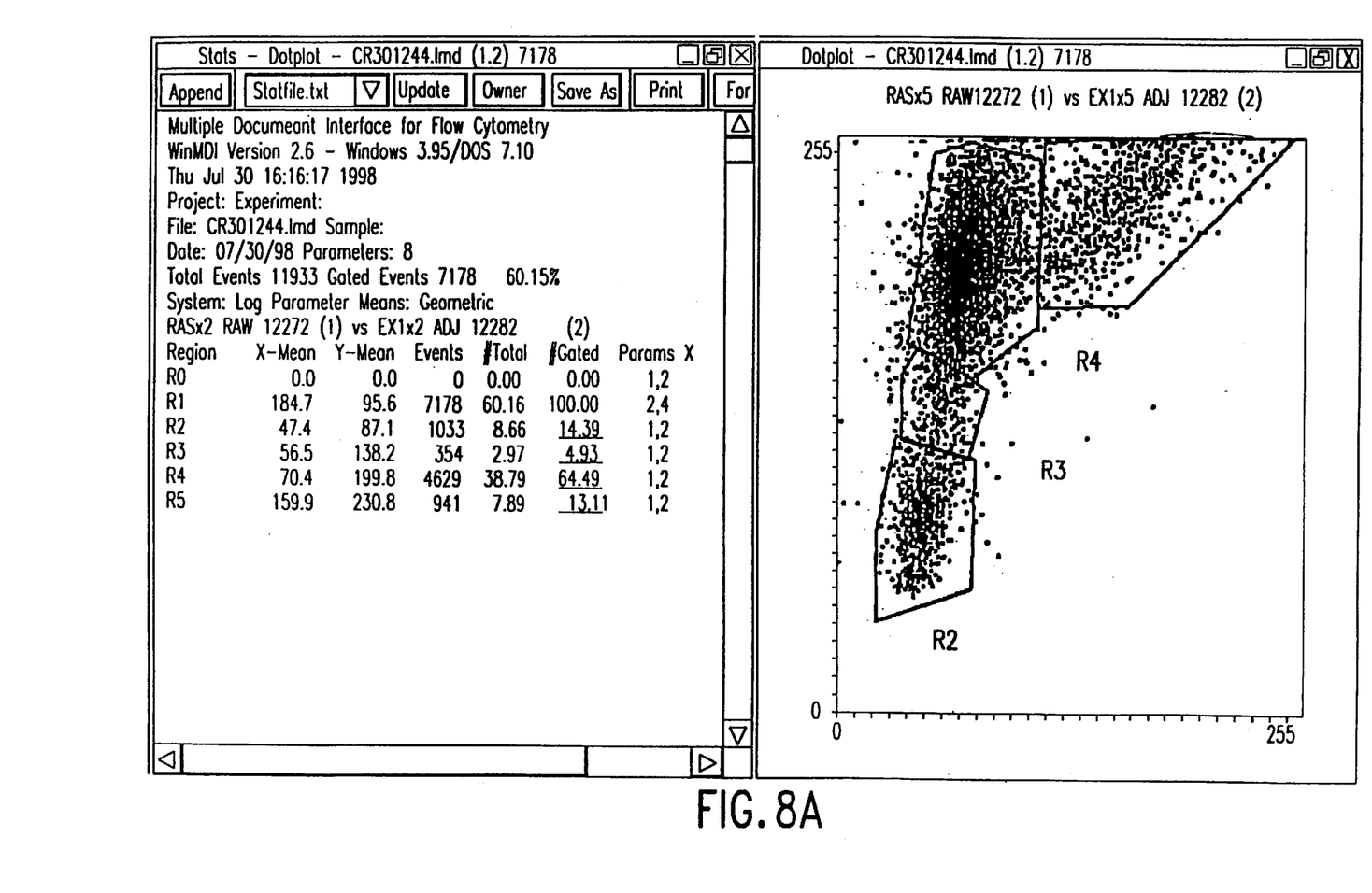
FIG. 8A is a graphical representation of 10% canine eosinophil data employing the prior art.
Figure 8B:
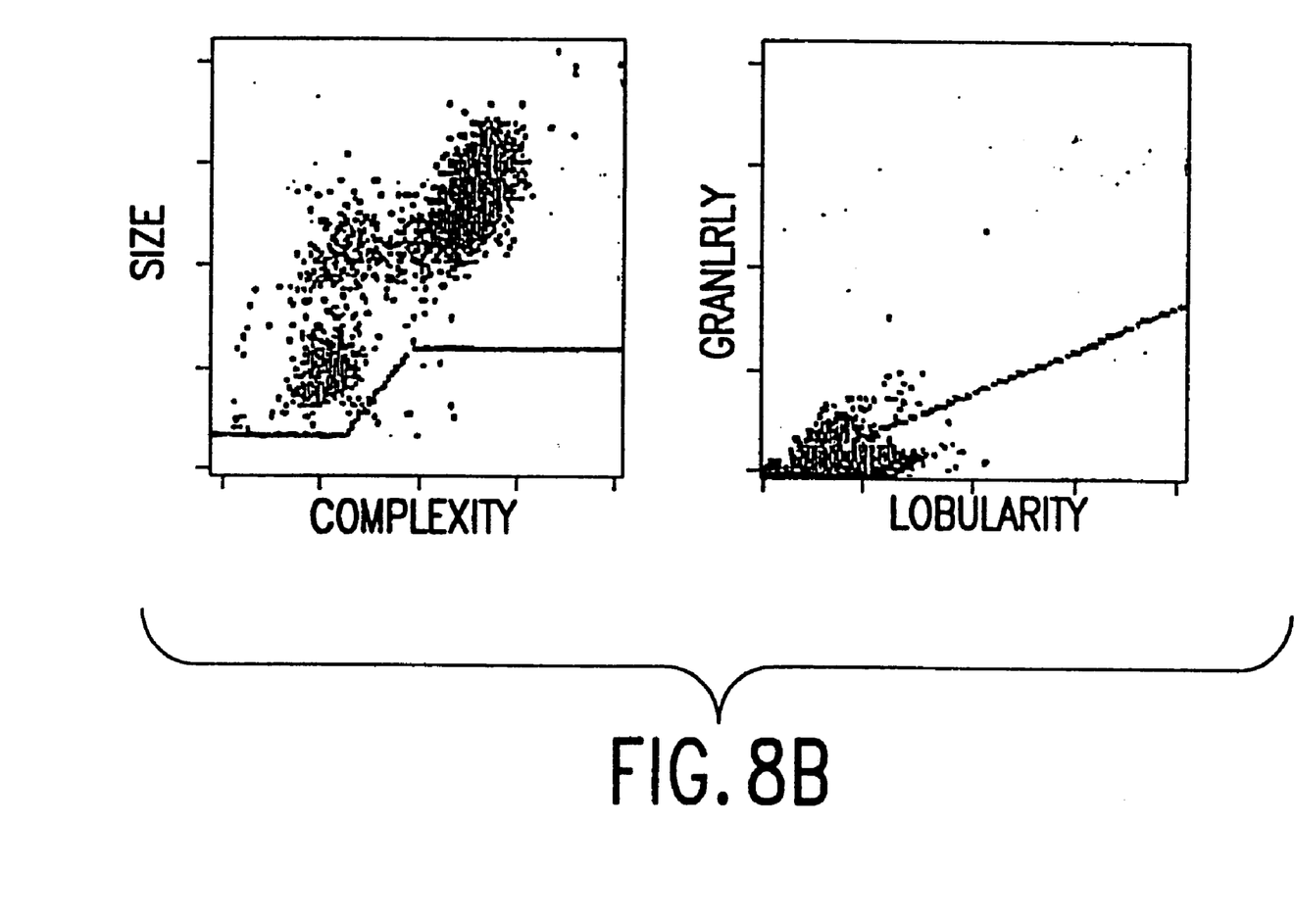
FIG. 8B is a graphical representation of 10% canine eosinophil data employing the present invention.
Figure 9A:
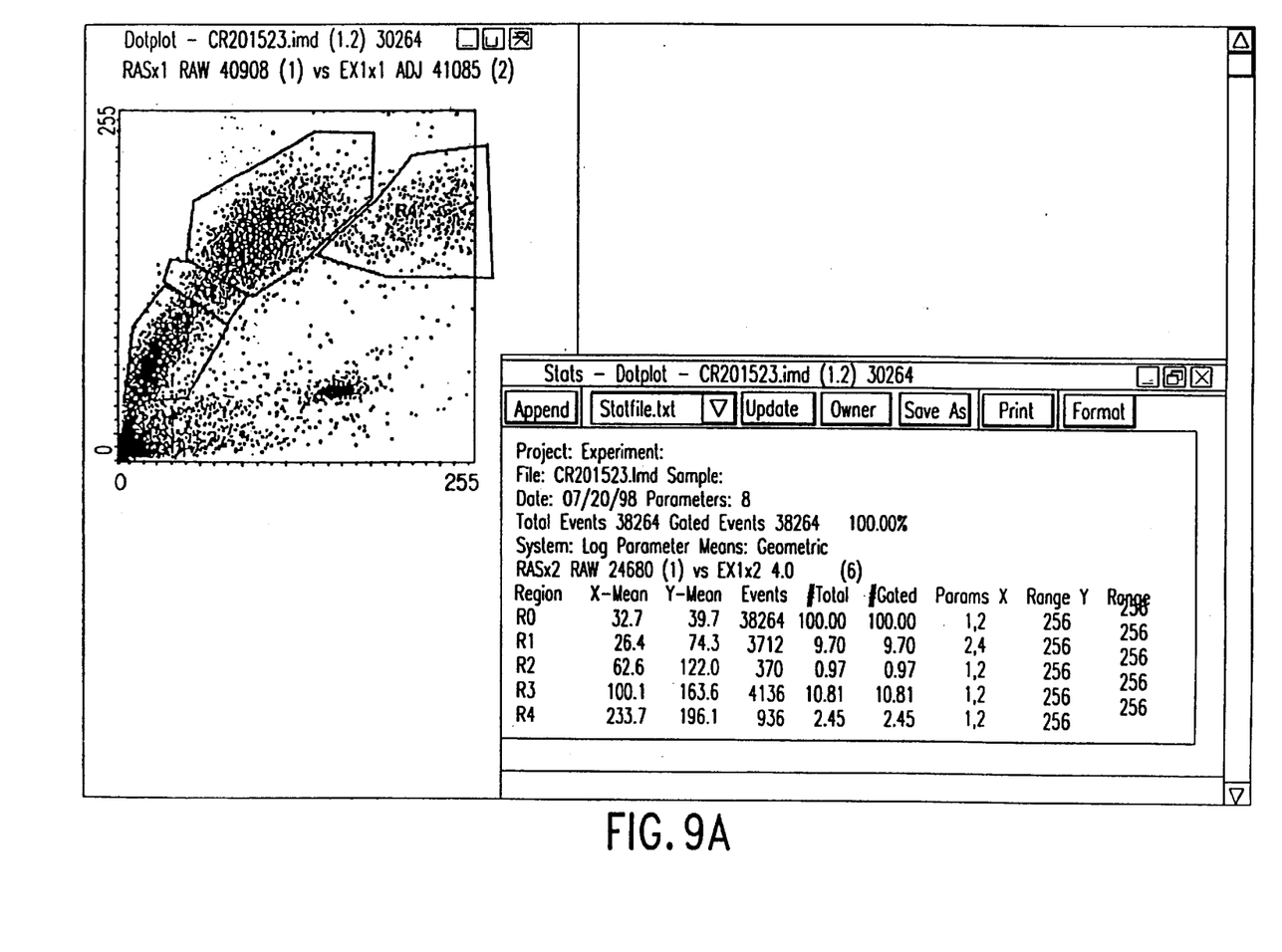
FIG. 9A is a graphical representation of human eosinophil data employing the prior art.
Figure 9B:
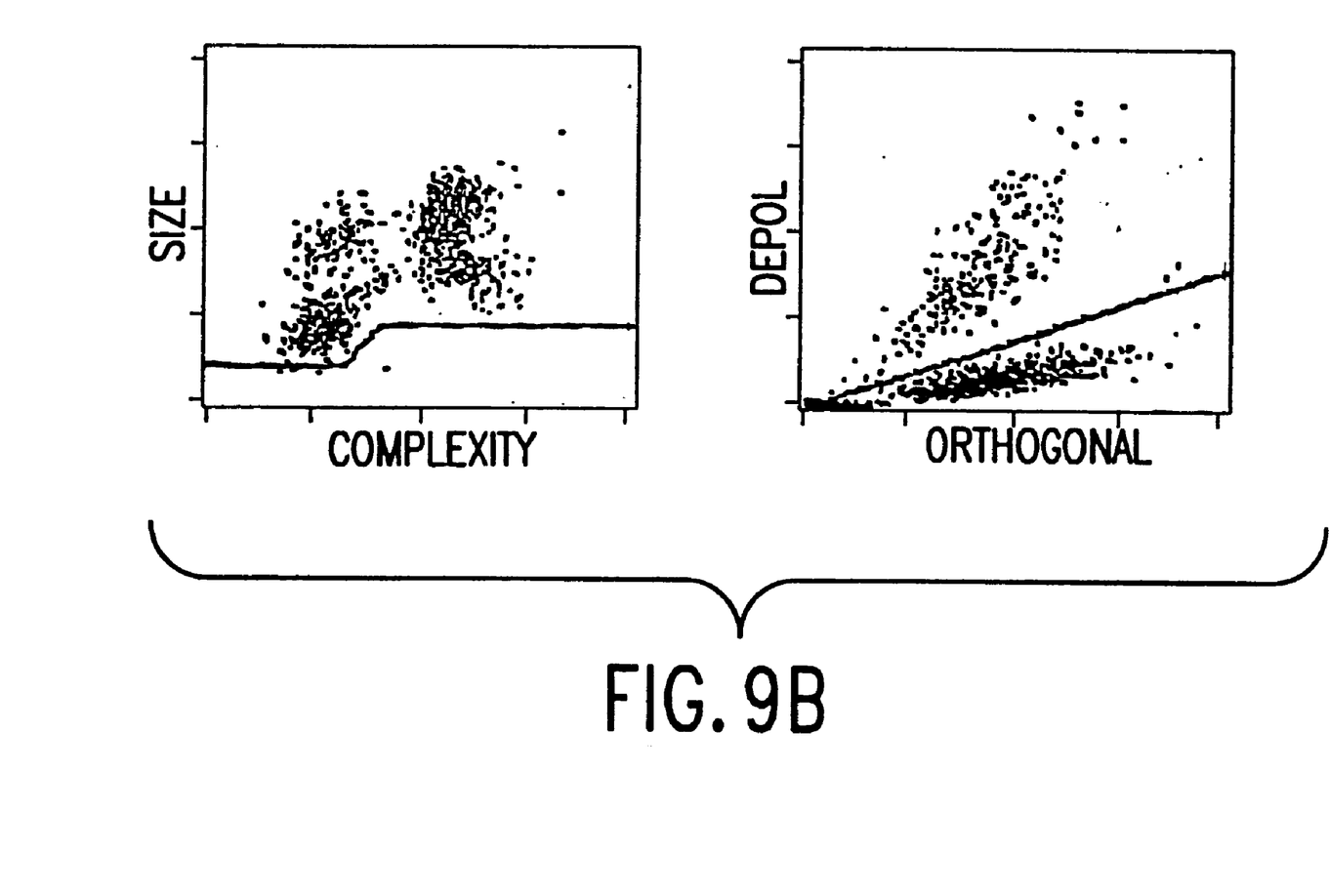
FIG. 9B is a graphical representation of human eosinophil data employing the present invention.

As shown in FIG. 4 eosinophils, a subset of leukocytes (white blood cells), depolarize the right angle of scattered light quantified by the above configuration to a greater degree than other leukocytes. FIG. 4 is a graphical representation having the output of polarized light detector 14 as one axis and the output of depolarized light detector 16 as the axis . While the above invention does provide some useful data regarding leukocytes, and more specifically eosinophils, as shown in FIGS. 6B, 7B, 7B and 9B, the cluster points within the eosinophil cluster (the cluster points above the angled threshold line on the graphical representation having "DEPOL" as one axis and "ORTHAGONAL" as the other axis) are quite condensed. The dense nature of the points within the eosinophil cluster results in difficulty for the computer software programs that ascertain and identify clusters to accurately identify eosinophil clusters. Additionally, this prior art configuration requires expensive optical devices such as photo multiplier tubes, and lens 6, first polarization amplifier 10 and second polarization amplifier 12.

A need thus exists for a flow cytometer apparatus and related method in which the cell cluster points are less dense for ease of characterization of the different cell clusters. A need also exists for the above apparatus and method which has fewer and less expensive components.

SUMMARY OF THE INVENTION

The high numerical aperture flow cytometer of the present invention includes a flow cell and a laser input. The laser input emits a beam of light that is oriented substantially orthogonally to the flow of blood cells through the flow cell such that laser light impinges upon the blood cells as they pass through the flow cell. Unlike the prior art, the laser light emitted by the laser input need not be polarized for analysis of the cells according to the present invention. A portion of the beam from the laser input that impinges upon the blood cells in the flow cell is scattered at a substantially right angle to the beam of laser input ("right angle scatter light"). A second portion of the beam from the laser input that impinges upon the cells in the flow cell is scattered at a much lower angle than 90°. This scatter is termed "low angle forward scatter light" and has an angle of from about 2° to about 5° from the orientation of the original beam from laser input. A right angle scatter light detector is oriented to receive the previously mentioned right angle scatter light. The right angle scatter light detector is preferably located about 2 millimeters from the blood cells in the flow cell. An important aspect of the present invention is that, at the distance of about 2 millimeters from the blood cells, the right angle scatter light detector collects a cone of scattered light of at least 100° or greater, and preferably 130° or greater. It is this larger light cone value over the prior art light cone of about 72° that results in the greater cluster separation in the present invention due to the larger signal gathered. In contrast, the smaller 72° cone of the prior art results in missed signals and lesser cluster separation.

A low angle forward scatter light detector is oriented to capture the previously mentioned low angle forward scatter light oriented at about 2° to about 5° from the beam of the laser input.

In one embodiment of the present invention, both right angle scatter light detector and low angle forward scatter light detector are employed in order to produce a 2-dimensional cytrogram. However, it should be noted that in another embodiment of the present invention, only right angle scatter light detector is employed, low angle forward scatter light detector is not employed, and characterization of eosinophils is possible.

BRIEF DESCRIPTION OF THE DRAWINGS

These and other objects and features of the invention will become more fully apparent when the following detailed description of the invention is read in conjunction with the accompanying drawings.

DETAILED DESCRIPTION OF THE PREFERRED EMBODIMENTS

Figure 2:
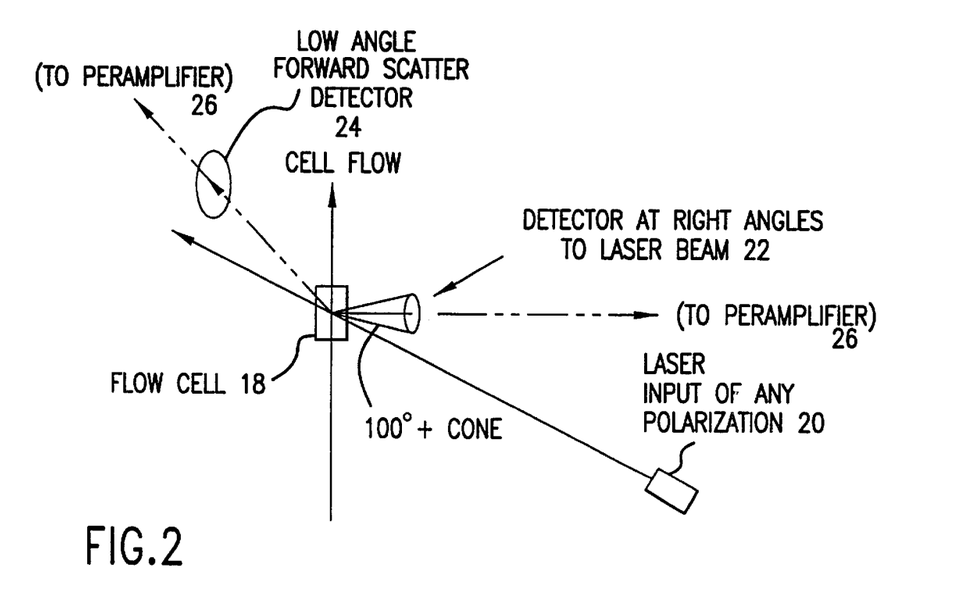
FIG. 2 is a schematic representation of the electro-optical components of the present invention.

Referring to FIG. 2, the high numerical aperture flow cytometer of the present invention includes a flow cell 18, which is preferably a quartz flow cell manufactured by Opco Laboratories of Fitchburg, Mass. Preferably flow cell 18 has a flow length of about 1 centimeter and a cross section of 4 millimeter by 4 millimeter. Cells from, for example, blood or the like, flow substantially one by one through flow cell 18 during analysis. Laser input 20 emits a beam of light that is oriented substantially orthogonally to the flow of blood cells through flow cell 18 such that laser light impinges upon the blood cells as they pass through flow cell 18. Unlike the prior art, the laser light emitted by laser input 20 need not be polarized for analysis of the cells according to the present invention. Laser input 20 maybe for example a 635 manometer semiconductor diode laser with an output power of 10 milliwatts, model No. HL6320G manufactured by Hitachi and available from Thor Labs, Inc. of Newton, N.J. A portion of the beam from laser input 20 that impinges upon the blood cells in flow cell 18 is scattered at a substantially right angle to the beam of laser input 20 ("right angle scatter light"). A second portion of the beam from laser input 20 that impinges upon the cells in flow cell 18 is scattered at a much lower angle than 90°. This scatter is termed "low angle forward scatter light" and has an angle of from about 2° to about 5° from the orientation of the original beam from laser input 20. Right angle scatter light detector 22 is oriented to receive the previously mentioned right angle scatter light. Right angle scatter light detector is preferably located about 2 millimeters from the blood cells in the flow cell 18. An important aspect of the present invention is that, at the distance of about 2 millimeters from the blood cells, right angle scatter light detector 22 collects a cone of scattered light of at least 100° or greater, and preferably 130° or greater. It is this larger light cone value over the prior art light cone of about 72° that results in the greater cluster separation in the present invention due to the larger signal gathered. In contrast, the smaller 72° cone of the prior art results in missed signals and lesser cluster separation.

Low angle forward scatter light detector 24 is oriented to capture the previously mentioned low angled forward scatter light oriented at about 2° to about 5° from the beam of laser input 20. Both right angle scatter light detector 22 and low angle forward scatter light detector 24 can be, for example, silicone PIN photodiodes Model No. S5106PIN manufactured by Hamamatsu Corp. of Bridgewater, N.J.

In one embodiment of the present invention, both right angle scatter light detector 22 and low angle forward scatter light detector 24 are employed in order to produce a 2-dimensional cytrogram. However, it should be noted that in another embodiment of the present invention, only right angle scatter light detector 22 is employed, low angle forward scatter light detector 24 is not employed, and characterization of eosinophils is possible.

While the electro-optical elements of FIG. 2 have been described above using specific components, it will readily be apparent to one skilled in the art that different components can be employed to achieve the desired results described above. More specifically, reference is made to Practical Flow Cytometry $3^{rd}$ Ed. 1995 by Howard M. Shapiro, Wiley-Liss Publisher, ISBN No. 0-471-30376-3, which is incorporated herein by reference.

Figure 3:
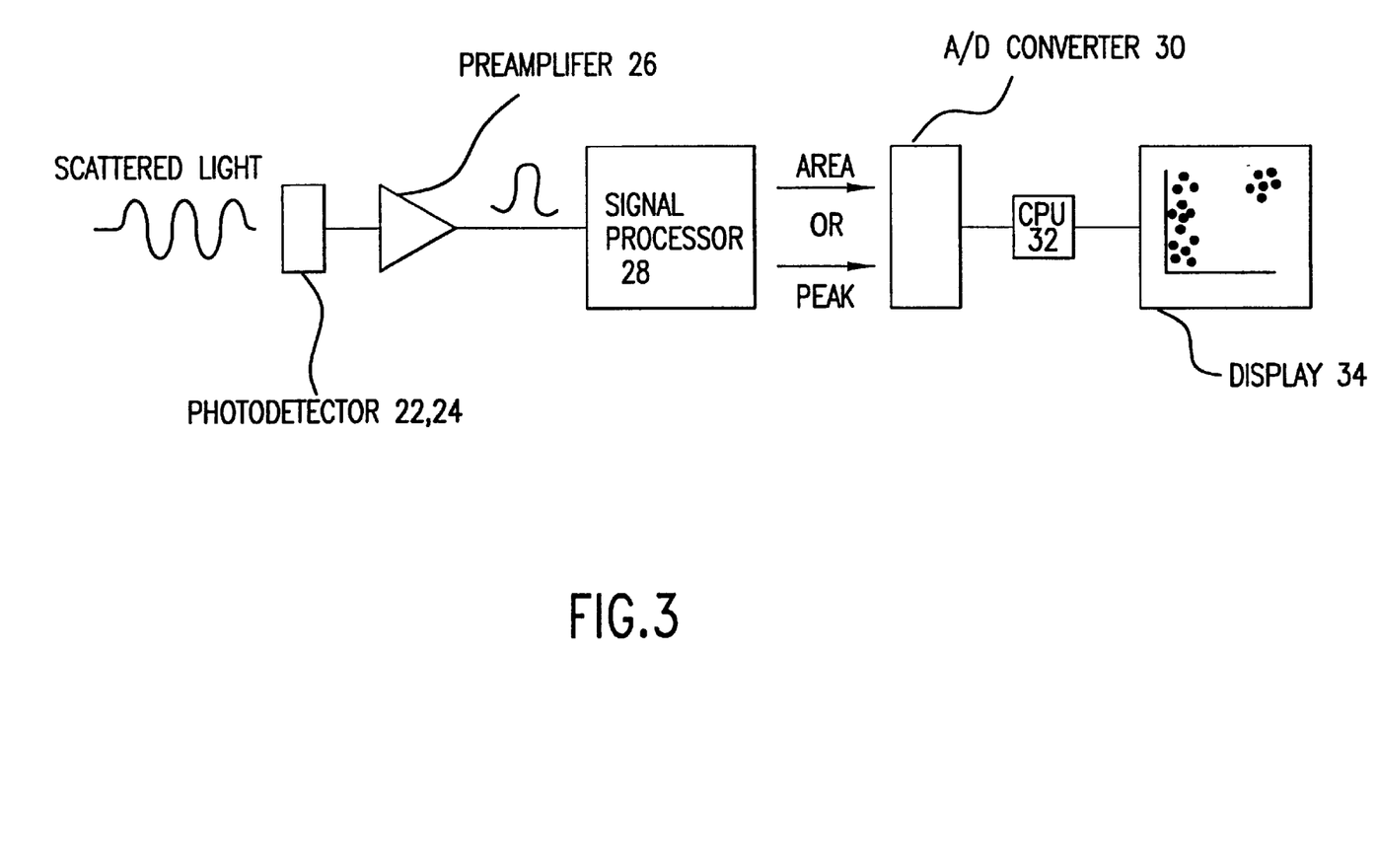
FIG. 3 is a block diagram of the electronic processing components of the present invention.

Referring to FIG. 3, the electrical outputs from right angle scatter light detector 22 and low angle forward scatter light detector 24, which may be in voltage or current form, for example, are amplified by preamplifier 26 and then sent to signal processor 28. Signal processor 28 measures the area under the voltage or current curve, or measures the peak of the voltage or current curve, received from right angle light scatter detector 22 and/or low angle forward scatter light detector 24. The data from signal processor 28 is converted by analog to digital converter 30. The digital data is next processed by central processing unit 32 based on software programs to display the data in graphical representation on display 34. It will be readily apparent to those skilled in the art that the signal amplification, processing, conversion and display can be accomplished by many well known methods, including but not limited to those disclosed in Practical Flow Cytometry $3^{rd}$ Ed. by Howard M. Shapiro, 1995 Wiley-Liss Publishers, ISBN No. 0-471-30376-3, incorporated herein by reference.

Figure 5:
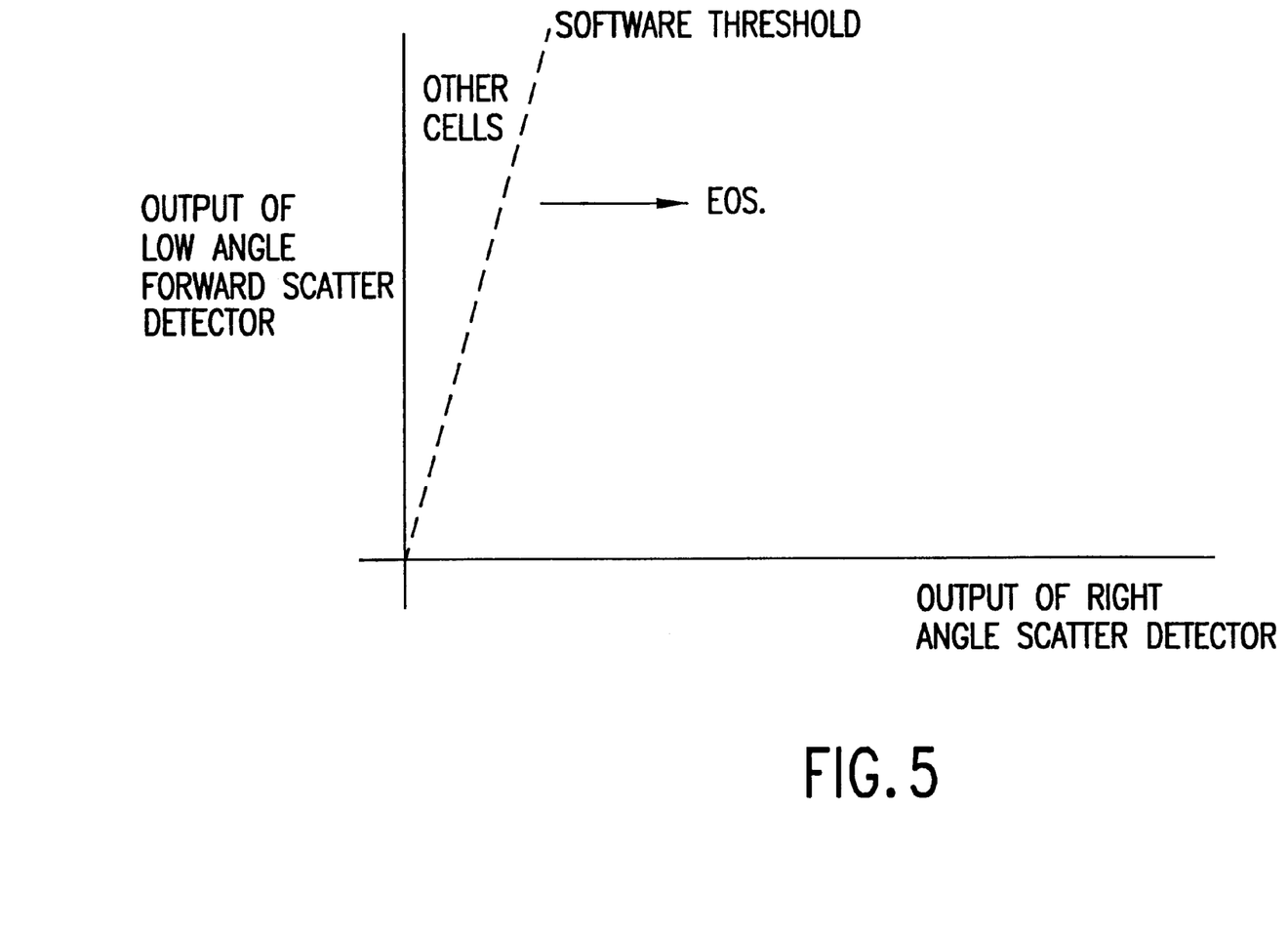
FIG. 5 is a graphical representation of the separation of eosinophils and other white blood cell components based on light scatter in the present invention.

Referring to FIG. 5, the output of the data from the flow cytometer of the present invention is shown. FIG. 5 has the output of right angle scatter light detector 22 as one axis and the output of low angle forward scatter light detector 24 as the other axis. Eosinophils are located to the right of the software threshold line and, as shown in FIGS. 6A, 7A, 8A, and 9A, produce cluster points that are less concentrated than are those of the prior art. Computer software programs employed to identify clusters based on cluster points can thus do so more reliably with the present invention.

Next referring to FIGS. 6A, 6B, 7A, 7A, 7B, 8A, 8B, 9A and 9B, graphical representations of leukocyte identification is shown, with specific reference to eosinophil identification. The data of FIGS. 6A, 7A, 8A, and 9A was employed using the apparatus of the present invention. In FIGS. 6A, 7A, 8A, and 9A the term R2 denotes primarily lymphocytes, R3 denotes primarily monocytes, R4 denotes primarily neutrophils and R5 denotes primarily eosinophils. FIGS. 6B, 7B, 8B, and 9B pertain to data employing an apparatus substantially disclosed in U.S. Pat. No. 5,017,497. Whole blood samples of either canine or human blood were prepared as follows before analyzing with the apparatus of present invention or the prior art. The whole blood sample was diluted 10 to 1 in phosphate buffered saline. Then 40 microliters of the phosphate buffered saline treated whole blood sample was mixed with 1,200 microliters of a lysing solution. The lysing solution consisted of 8.3 grams of ammonium chloride, 1 gram of potassium bicarbonate, 0.37 grams tetrasodium EDTA per liter of lysing solution. The whole blood sample was lysed for 20 minutes to one-half of an hour. It will be readily understood by those skilled in the art that lyse time can readily be reduced to between 30 seconds and one minute.

A good correlation exists between the eosinophil of the present invention of FIGS. 6A, 7A, 8A and 9A with the eosinophil data of the DEPOL/ORTHOGONAL graphical representation of the prior art as shown in FIGS. 6B, 7B, 8B and 9B. More specifically, regarding FIGS. 6A and 6B, the eosinophil value for the present invention is 2.1% and for the prior art is 2.0%. Regarding FIGS. 7A and 7B, the eosinophil data for the present invention is 7.6% and for the prior art is 8.2%. Regarding FIGS. 8A and 8B the eosinophil data for the present invention is 13.1% and for the prior art is 9.8%. Regarding FIGS. 9A and 9B the eosinophil data for the present invention is 10.8% and for the prior art is 14.6%. For all of the above graphical representations of the present invention, FIGS. 6A, 7A, 8A and 9A an eosinophil cluster is present at R5. Regarding the prior art data of FIGS. 6B, 7B and 8B the SIZE/COMPLEXITY graphical representation shows no eosinophil cluster, while the graphical representation of FIG. 9B does show a cluster.

A comparison of the data of the present invention from FIGS. 6A, 7A, 8A and 9A with the prior art data of FIGS. 6B, 7B, 8B and 9B show a marked decreased density or concentration of the cluster points within the eosinophil clusters. The separation of these cluster points allows the software programs that locate and identify different clusters to more readily locate and identify the clusters produced by the apparatus and method of the present invention compared to those of the prior art.

While the invention has been described with reference to particular embodiments and applications, it will be appreciated that various embodiments and applications based on the teaching of the present invention are possible.

What is claimed is:

1. A flow cytometer, comprising:
   a flow cell;
   a laser input, said laser input emitting a beam of light that is oriented substantially orthogonally to a direction of flow of blood cells through said flow cell;
   a right angle scatter light detector, said right angle scatter light detector being effective to collect a cone of unfiltered right angle scattered light of at least 100° and convert said right angle scattered light into a right angle scattered light signal; and
   a signal processor, said signal processor being effective to distinguish eosinophils from other leukocytes on the basis of said right angle scattered light signal.

2. The flow cytometer of claim 1, wherein said right angle scatter light detector is located at a distance of about 2 millimeters from said flow cell.

3. The flow cytometer of claim 1, further comprising at least one low angle forward scatter light detector, said low angle forward scatter light detector being effective to collect low angle forward scattered light at an angle between about 2° to about 5° from said beam.

4. The flow cytometer of claim 1, wherein said right angle scatter light detector is effective to collect a cone of unfiltered right angle scattered light of at least 130°.

5. The flow cytometer of claim 1, further comprising:
   a low angle forward scatter light detector, said low angle forward scatter light detector being effective to collect low angle forward scattered light at an angle between about 2° to about 5° from said beam; and
   a right angle scatter light detector located at a distance of about 2 millimeters from said flow cell and effective to collect a cone of unfiltered right angle scattered light of at least 130°.

6. A method for particle discrimination by light scattering, comprising the steps of:
   flowing a liquid containing biological cells through a flow cell;
   directing a beam of light in a direction that contacts said biological cells in said flow cell and is substantially orthogonal to a direction of flow of said biological cells through said flow cell;
   detecting a cone of unfiltered right angle scattered light of at least 100°;
   converting said detected unfiltered right angle scattered light into a right angle scattered light signal; and
   identifying eosinophils present among said biological cells on the basis of said right angle scattered light signal.

7. The method of claim 6, wherein said step of detecting is performed by a right angle scatter light detector located at a distance of about 2 millimeters from said flow cell.

8. The method of claim 6, further comprising collecting low angle forward scattered light at an angle between about 2° to about 5° from said beam of light.

9. The method of claim 6, further comprising detecting a cone of unfiltered right angle scattered light of at least 130°.

10. The method of claim 6, further comprising:
    detecting said cone of unfiltered right angle scattered light by using a right angle scatter light detector located at a distance of about 2 millimeters from said flow cell;
    collecting low angle forward scattered light at an angle between about 2° to about 5° from said beam of light; and
    detecting a cone of unfiltered right angle scattered light of at least 130°.

11. A flow cytometer, comprising:
    a flow cell;
    a laser input, said laser input emitting a beam of light that is oriented substantially orthogonally to a direction of flow of blood cells through said flow cell;
    a right angle scatter light detector, said right angle scatter light detector being effective to collect a cone of right angle scattered light of at least 100° and convert said right angle scattered light into a right angle scattered light signal; and
    a signal processor, said signal processor being effective to distinguish eosinophils from other leukocytes on the basis of said single right angle scattered light signal.

12. The flow cytometer of claim 11, wherein said right angle scatter light detector is located at a distance of about 2 millimeters from said flow cell.

13. The flow cytometer of claim 11, further comprising at least one low angle forward scatter light detector, said low angle forward scatter light detector being effective to collect low angle forward scattered light at an angle between about 2° to about 5° from said beam.

14. The flow cytometer of claim 11, wherein said right angle scatter light detector is effective to collect a cone of unfiltered right angle scattered light of at least 130°.

15. The flow cytometer of claim 11, further comprising:
a low angle forward scatter light detector, said low angle forward scatter light detector being effective to collect low angle forward scattered light at an angle between about 2° to about 5° from said beam; and
a right angle scatter light detector located at a distance of about 2 millimeters from said flow cell and effective to collect a cone of unfiltered right angle scattered light of at least 130°.

16. A method for particle discrimination by light scattering, comprising the steps of:
flowing a liquid containing biological cells through a flow cell;
directing a beam of light in a direction that contacts said biological cells in said flow cell and is substantially orthogonal to a direction of flow of said biological cells through said flow cell;
detecting a cone of right angle scattered light of at least 100°;
converting said detected right angle scattered light into a single right angle scattered light signal; and
identifying eosinophils present among said biological cells on the basis of said single right angle scattered light signal.

17. The method of claim 16, wherein said step of detecting is performed by a right angle scatter light detector located at a distance of about 2 millimeters from said flow cell.

18. The method of claim 16, further comprising collecting low angle forward scattered light at an angle between about 2° to about 5° from said beam of light.

19. The method of claim 16, further comprising detecting a cone of right angle scattered light of at least 130°.

20. The method of claim 16, further comprising:
detecting said cone of right angle scattered light by using a right angle scatter light detector located at a distance of about 2 millimeters from said flow cell;
collecting low angle forward scattered light at an angle between about 2° to about 5° from said beam of light; and
detecting a cone of right angle scattered light of at least 130°.

* * * * *

UNITED STATES PATENT AND TRADEMARK OFFICE
CERTIFICATE OF CORRECTION

PATENT NO. : 6,320,656 B1  
DATED : November 20, 2001  
INVENTOR(S) : Ferrante et al.

Page 1 of 1

It is certified that error appears in the above-identified patent and that said Letters Patent is hereby corrected as shown below:

Column 1,  
Line 4, "FIELD OF THE INVENTION", insert -- This application claims the benefit of US Provisional Patent Application Serial No. 60/120,804, filed February 19, 1999. --  
Lines 22-23, should read -- FIG. 1 of the present application illustrates the apparatus disclosed in the '497 Patent. --  
Line 66, "the axis ." should read -- the other axis. --.

Column 2,  
Line 1, "as shown in FIGS. 6B, 7B, 7B and 9B," should read -- as shown in FIGS. 6B, 7B, 8B and 9B, --.  
Line 57, "cytrogram" should read -- cytogram --.

Column 3,  
Lines 15, 19, 23 and 27, "the prior art" should read -- the present invention --.  
Lines 17, 21, 25 and 29, "the present invention" should read -- the prior art --.  
Line 47, "manometer" should read -- nanometer --.

Column 4,  
Line 15, "2-dimensional cytrogram" should read -- 2-dimensional cytogram --.  
Line 58, "Next referring to FIGS. 6A, 6B, 7A, 7A, 7B, 8A, 8B, 9A" should read -- Next referring to FIGS. 6A, 6B, 7A, 7B, 8A, 8B, 9A --.

Column 5,  
Line 14, "between the eosinophil of the" should read -- between the eosinophil data of the --.

Signed and Sealed this

Thirtieth Day of July, 2002

Attest:

JAMES E. ROGAN  
Attesting Officer     Director of the United States Patent and Trademark Office